United States Patent [19]

Gerber et al.

[11] Patent Number: 5,653,988

[45] Date of Patent: Aug. 5, 1997

[54] SHOWER OIL

[75] Inventors: Bozena Gerber; Otto Stelling; Robert Schmucker, all of Hamburg; Hartmut Schmidt-Lewerkühne, Schenefeld, all of Germany

[73] Assignee: Beiersdorf Aktiengesellschaft, Hamburg, Germany

[21] Appl. No.: 497,681

[22] Filed: Jun. 30, 1995

[30] Foreign Application Priority Data

Jul. 9, 1994 [DE] Germany .................. 44 24 210.7

[51] Int. Cl.$^6$ .................................................. A61K 7/48
[52] U.S. Cl. .................. 424/401; 514/844; 514/846; 514/975
[58] Field of Search ............... 424/401; 514/844, 514/846, 975

[56] References Cited

U.S. PATENT DOCUMENTS 4,921,874  5/1990  Franke et al. .................. 514/552

FOREIGN PATENT DOCUMENTS

| 534462 | 4/1981 | Australia ............... 424/401 |
| 1467963 | 3/1969 | Germany . |
| 279049 | 2/1970 | Germany . |
| 2943202 | 3/1981 | Germany . |
| 3413563 | 10/1985 | Germany . |

OTHER PUBLICATIONS

Harry's Cosmeticology by Ralph Harry, pp. 230–233, 240–243 1973.

Cosmetic and Toiletry Formulations by E.W. Flick, pp. 30–31, 58–59, 65–71 1989.

*Primary Examiner*—Jyothsna Venkat
*Attorney, Agent, or Firm*—Sprung Horn Kramer & Woods

[57] ABSTRACT

Cosmetic or dermatological shower formulations, characterized by
(a) containing a content of not more than 55% by weight, based on the total weight of the formulations, of one or more surfactants selected from the group of
fatty alcohol ethoxylates, fatty alcohol sulphates, amides of fatty alcohol sulphates, fatty alcohol ether sulphates, amides of fatty alcohol ether sulphates, fatty acid monoethanolamides, fatty acid diethanolamides,
(b) a content of not less than 45% by weight, based on the total weight of the formulations, of one or more oil components selected from the group of oils with a high content of triglycerides of saturated and/or unsaturated, branched and/or unbranched fatty acids,
or exclusively such triglycerides,
(c) optionally containing further surfactants,
(d) optionally containing further cosmetic or pharmaceutical auxiliaries, additives and/or active substances,
(e) where the formulations are essentially anhydrous.

5 Claims, No Drawings

SHOWER OIL

The present invention relates to cosmetic cleansing formulations, preferably for use as shower product.

Formulations of this type are known per se. They essentially comprise surface-active substances or mixtures of substances which are offered to the user in various formulations. Formulations of this type are generally distinguished by a more or less high water content, but can also be, for example, in the form of a concentrate.

In general, products intended for the shower bath differ scarcely or not at all from bath tub formulations, apart from the fact that higher viscosity products which do not run out of the hand after removal from the container are preferred for shower formulations. This is of less practical importance for bath tub formulations.

Even with a simple bath in water without added surfactants there is initial swelling of the stratum corneum of the skin, and the degree of this swelling depends, for example, on the duration of the bath and its temperature. At the same time, water-soluble substances, e.g. water-soluble components of dirt but also substances which belong to the skin and which are responsible for the water-binding capacity of the stratum corneum, are washed off or out. In addition, sebaceous matter is also dissolved and washed out to a certain extent by surface-active substances belonging to the skin. This results, after initial swelling, in subsequent marked drying out of the skin, which may also be enhanced by detergent additives.

When the skin is healthy, these processes are generally of no significance because the protective mechanisms of the skin are able to compensate without difficulty such slight disturbances of the upper layers of skin. However, even in the case of non-pathological deviations from the normal status, e.g. due to environmentally-related wear damage or irritation, light damage, skin ageing etc., the protective mechanism of the skin surface is impaired. In some circumstances it is no longer able by itself to carry out its task and must be regenerated by external measures.

Bath oil formulations Of various types are known in the state of the art, it being possible to alter the properties of the fat or oil phase by adding surface-active substances. It is moreover possible to formulate, depending on the nature and amount of the constituents chosen, formulations which give on the surface of the bath water either spreading oil films, oil-in-water systems or else total solubilizates. Foaming formulations, but also low-foaming or non-foaming formulations are possible.

The functionality of such formulations is generally confined in the case of bath oil or cream bath oil formulations to lubrication or superfatting of the topmost layers of skin.. European published specification 120 224 does in fact describe bath oil formulations containing active substances with a content of 38.75% by weight of soya oil, 2.00% by weight of castor oil, 37.00% by weight of liquid petrolatum. Disclosed as emulsifier are polyethylene glycol mono- and diesters in concentrations of about 10–12% by weight.

A considerable disadvantage of the state of the art is that such bath formulations are present in very great dilution (contents of a bath tub: several hundred liters of water in the individual case). This must be taken into account by special care in the formulation or use of large amounts of the bath oil formulation to be used.

Unknown in the state of the art are surfactant-containing shower formulations with a high oil content, which could be called shower oils, probably primarily because the skilled person necessarily assumed that formulations with a high oil content would display virtually no foaming effect or else no care effect.

The inappropriate use of a foaming bath oil formulation as shower formulation is no alternative for this. This use is inappropriate because such formulations produce negligible foam.

It was thus an object of the present invention to remedy this deficiency of the state of the art. It was furthermore an object of the invention to provide shower bath formulations which, on the one hand, have a great care effect without, on the other hand, the cleaning effect being inferior thereto.

It has emerged, astonishingly, that cosmetic or dermatological shower formulations characterized by (a) containing a content of not more than 55% by weight, based on the total weight of the formulations, of one or more surfactants selected from the group of fatty alcohol ethoxylates, fatty alcohol sulphates, amides of fatty alcohol sulphates, fatty alcohol ether sulphates, amides of fatty alcohol ether sulphates, fatty acid monoethanolamides, fatty acid diethanolamides, and (b) a content of not less than 45% by weight, based on the total weight of the formulations, of one or more oil components selected from the group of oils with a high content of triglycerides of saturated and/or unsaturated, branched and/or unbranched fatty acids, or exclusively such triglycerides, (c) optionally containing further surfactants, (d) optionally containing further cosmetic or pharmaceutical auxiliaries, additives and/or active substances, (e) where the formulations are essentially anhydrous, comply with the objects on which the invention is based in an extremely satisfactory manner. The formulations according to the invention have very good foam production, high cleansing power and a high degree of regenerating action in respect of the general condition of the skin. In particular, the formulations according to the invention act to smooth the skin, reduce the feeling of dryness of the skin and make the skin supple.

The fatty alcohol sulphates and fatty alcohol ether sulphates to be beneficially used according to the invention advantageously have the following structure:

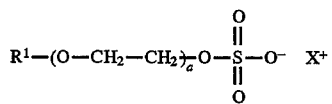

In this, a can assume values from 0 to 10, advantageously 1 to 5. $R^1$ is selected from the group of branched and unbranched alkyl groups with 6 to 24 carbon atoms.

$X^+$ is selected from the group of alkali metal ions and from the group of ammonium ions which are substituted by one or more alkyl and/or one or more hydroxyalkyl radicals.

The amides of the fatty alcohol sulphates or of the fatty alcohol ether sulphates to be beneficially used according to the invention advantageously have the following structure:

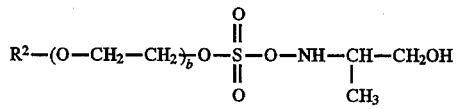

In this, b can assume values from 0 to 10, advantageously 1 to 5. $R^2$ is selected from the group of branched and unbranched alkyl groups with 6 to 24 carbon atoms.

The preferred fatty alcohol ether sulphate is MIPA laureth sulphate.

The fatty alcohol ethoxylates to be beneficially used according to the invention advantageously have the following structure:

$$R^3-(O-CH_2-CH_2-)_c-OH$$

In this, c can assume values from 1 to 45, preferably from 1 to 10. $R^3$ is selected from the group of branched and unbranched alkyl groups with 6 to 24 carbon atoms.

The preferred fatty alcohol ethoxylate is laureth-4.

The fatty acid mono- and diethanolamides to be beneficially used according to the invention advantageously have the following structures:

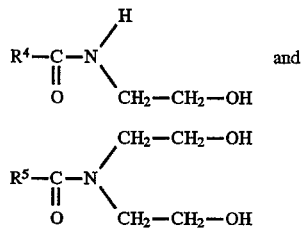

$R^4$ and $R^5$ are for this purpose selected from the group of branched and unbranched alkyl groups and/or alkenyl groups with 6 to 24 carbon atoms.

The preferred fatty acid diethanolamide is coconut fatty acid diethanolamide (cocamide DEA). Natural coconut fatty acid contains as essential constituents 44–51% by weight of lauric acid, 13–18% by weight of myristic acid, 8–10% by weight of palmatic acid, 6–9% by weight of caprylic acid, 6–10% by weight of capric acid, 5–8% by weight of oleic acid, 1–3% by weight of stearic acid, 0–2% by weight of linoleic acid and 0–1% by weight of caproic acid.

It is very particularly preferred to employ mixtures of MIPA laureth sulphate, laureth-4 and coconut fatty acid diethanolamide. Such mixtures can be obtained, for example, under the name ZETESOL® 100 from Zschimmer & Schwarz Chemische Fabriken, Lahnstein/Rhein, or TEX-APON® WW 99 from Henkel KGaA, Düsseldorf.

The oils according to the invention are preferably selected from the group of triglycerides of the following structure:

```
H2C—O—R6
 |
HC—O—R7
 |
H2C—O—R8,
``` where $R^6$, $R^7$ and $R^8$ are, independently of one another, selected from the group of branched and unbranched alkylcarboxyl and alkenylcarbonyl groups with 12 to 24 carbon atoms. It is advantageous, where appropriate, for one or more aliphatic hydrogen atoms of the alkylcarboxyl or alkenylcarboxyl groups to be replaced by hydroxyl groups.

It is particularly advantageous for $R^6$, $R^7$ and/or $R^8$ to have 16 to 20 carbon atoms and to be selected from the group of mono- to triunsaturated carboxylic acid residues.

When $R^6$, $R^7$ and/or $R^8$ carry hydroxyl groups, the preferred alkenylcarboxyl radical is the ricinoleic acid residue.

It is particularly advantageous to select the oils according to the invention from the group of soya oil, sunflower oil, wheatgerm oil and castor oil.

Preferred formulations contain 0 to 60% by weight of soya oil and 0 to 60% by weight of wheatgerm oil and 0 to 60% by weight of sunflower oil, with the proviso that the total of the individual concentrations of these oils amounts to 30–60% by weight, furthermore castor oil in a concentration of 5–25% by weight, where these concentrations are in each case based on the total weight of the formulations.

It is true that the company brochure on "ZETESOL 100" discloses outline formulas which, besides the Zetesol 100 surfactant mixture to be used advantageously according to the invention, also contain sunflower oil, wheatgerm oil or soya oil. Although one formula is anhydrous, it contains 72% by weight of surfactant mixture and only 25% by weight of oils. The other formula contains 5% by weight of water, 68% by weight of surfactant mixture and only 15% by weight of oils.

Furthermore, the formulations of the state of the art comprise foaming bath oils with the disadvantages which have been described. The oil concentration is described already as "very high" at the place indicated. The state of the art has therefore assumed that a further increase in the oil concentration would be at least problematic. This prejudice is eliminated by the present invention.

It was particularly surprising that the formulations according to the invention produce, despite the high oil content, a rich creamy foam with extremely fine bubbles on use.

Besides the abovementioned surfactants, the compositions according to the invention contain water and, where appropriate, the additives customary in cosmetics, for example perfume, thickeners, solubilizers, colorants, deodorants, antimicrobial substances, lubricant agents, complexing and sequestering agents, pearlescent agents, plant extracts, vitamins, active substances and the like.

It is particularly advantageous to choose solubilizers from the group of polyoxyethylene/polyoxypropylene block copolymers. Block copolymers of this type are known under the name "poloxamers" and are distinguished by the following structure:

$$HO-(CH_2-CH_2-O)_x-(CH-CH_2-O)_y-(CH_2-CH_2-O)_z-OH$$
$$|$$
$$CH_3$$

In this, x advantageously assumes values between 2 and 20. y advantageously assumes values between 10 and 50. z advantageously assumes values between 2 and 20.

If formulations according to the present invention are intended to contain further surfactants besides the surfactants according to the invention, it is preferred to choose the concentration thereof to be no greater than 5% by weight based on the weight of the complete composition.

Antioxidants which can beneficially be used according to the invention are all antioxidants suitable or customary for cosmetic and/or dermatological applications.

The antioxidants are advantageously chosen from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. carotene, β-carotene, lycopene) and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, palmitoyl, oleyl, linoleyl, cholesteryl and glyceryl esters) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximine) in very small tolerated doses (e.g. pmol to μmol/kg), furthermore (metal) chelators (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitates, Mg ascorbyl phosphates, ascorbyl acetates), tocopherols and derivatives (e.g. vitamin E acetate), vitamin A and derivatives (vitamin A palmitate) and coniferyl benzoate of gum benzoin, rutinic acid and derivatives thereof, ferulic acid and derivatives thereof, butylated hydroxytoluene, butylated hydroxyanisole, nordihydroguaiaretic acid, trihydroxybutyrophenone, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide) and the derivatives suitable according to the invention (salts, esters, ethers, sugars, nucleotides, nucleosides, peptides and lipids) of these active substances mentioned.

It is possible and particularly advantageous for the purpose of the present invention to employ oil-soluble antioxidants.

The amount of the antioxidants (one or more compounds) in the formulations is preferably 0.001 to 30% by weight, particularly preferably 0.05–20% by weight, in particular 1–10% by weight, based on the total weight of the formulation.

Where vitamin E and/or derivatives thereof represent the antioxidant(s), it is advantageous to select the relevant concentrations thereof from the range 0.001–10% by weight, based on the total weight of the formulation.

Where vitamin A or vitamin A derivatives or carotenes or derivatives thereof represent the antioxidant(s), it is advantageous to select the relevant concentrations thereof from the range 0.001–10% by weight based on the total weight of the formulation.

The following examples are intended to illustrate the present invention. The numerical values in the examples mean percentages by weight based on the total weight of the relevant formulations.

| Example | 1 | 2 | 3 | 4 |
|---|---|---|---|---|
| soya oil | 54 | 40 | 37 | 42 |
| castor oil | 14 | 14 | 9 | 14 |
| ZETESOL 100 | 30 | 51 | 51 | 41 |
| poloxamer 101 | 2 | 2 | 2 | 2 |
| perfume, antioxidants, preservatives | q.s. | q.s. | q.s. | q.s. |

| Example | 5 | 6 | 7 | 8 |
|---|---|---|---|---|
| wheatgerm oil | 54 | 40 | 37 | 42 |
| castor oil | 14 | 14 | 9 | 14 |
| ZETESOL 100 | 30 | 51 | 51 | 41 |
| poloxamer 101 | 2 | 2 | 2 | 2 |
| perfume, antioxidants, preservatives | q.s. | q.s. | q.s. | q.s. |

| Example | 9 | 10 | 11 | 12 |
|---|---|---|---|---|
| sunflower oil | 54 | 40 | 37 | 42 |
| castor oil | 14 | 14 | 9 | 14 |
| ZETESOL 100 | 30 | 51 | 51 | 41 |
| poloxamer 101 | 2 | 2 | 2 | 2 |
| perfume, antioxidants, preservatives | q.s. | q.s. | q.s. | q.s. |

We claim:

1. A substantially anhydrous cosmetic or dermatological shower formulation by weight comprising (i) up to 55% of at least one of an amide of a fatty alcohol sulphate or an amide of a fatty alcohol ether sulphate of the formula

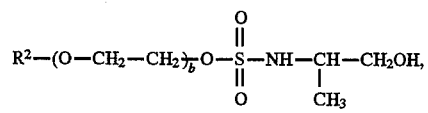

wherein (b) is a number from 0 to 10, and
   $R^2$ is an alkyl group with 6 to 24 carbon atoms, and (ii) at least 45% of at least one oil of acids selected from the group of saturated, unsaturated, branched and unbranched fatty acids, (iii) optionally further surfactants, and (iv) optionally further cosmetic or pharmaceutical auxiliaries, additives or active substances.

2. A shower formulation according to claim 1, wherein (ii) comprises a triglyceride of the formula

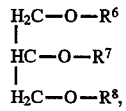

wherein $R^6$, $R^7$ and $R^8$ each independently is an alkylcarboxyl or alkenylcarboxyl group with 12 to 24 carbon atoms optionally substituted by hydroxyl.

3. A shower formulation according to claim 2, wherein $R^6$, $R^7$ and $R^8$ each independently has 16 to 20 carbon atoms and at least one of them is an alkenylcarboxyl radical.

4. A shower formulation according to claim 1, wherein (ii) comprises at least one member selected from the group consisting of soya oil, sunflower oil, wheatgerm oil and castor oil.

5. A shower formulation according to claim 1, containing 30 to 60% by weight of soya oil plus wheatgerm oil plus sunflower oil, plus 5 to 25% by weight of castor oil.

* * * * *

UNITED STATES PATENT AND TRADEMARK OFFICE
CERTIFICATE OF CORRECTION

PATENT NO. : 5,653,988
DATED : August 5, 1997
INVENTOR(S) : Gerber, et al.

It is certified that error appears in the above-indentified patent and that said Letters Patent is hereby corrected as shown below:

Col. 6, line 21   Delete " $R^2-(O-CH_2-CH_2)_b-O-\underset{\underset{O}{\|}}{\overset{\overset{O}{\|}}{S}}-NH-\underset{CH_3}{CH}-$ $CH_2OH$ " and substitute Col. 6, line 21   -- $R^2-(O-CH_2-CH_2)_b-O-\underset{\underset{O}{\|}}{\overset{\overset{O}{\|}}{S}}-O-NH-\underset{CH_3}{CH}-CH_2OH$ --

Signed and Sealed this

Seventh Day of July, 1998

Attest:

BRUCE LEHMAN

*Attesting Officer*    Commissioner of Patents and Trademarks